United States Patent [19]

Akai et al.

[11] Patent Number: 5,273,714
[45] Date of Patent: Dec. 28, 1993

[54] METHOD OF STERILIZING APPARATUS FOR SUPPLYING HYDROGEN PEROXIDE GAS

[75] Inventors: Tadao Akai; Kazuo Abe; Hiromichi Nishino, all of Tokushima, Japan

[73] Assignee: Shikoku Kakoki Co., Ltd., Tokushima, Japan

[21] Appl. No.: 912,856

[22] Filed: Jul. 14, 1992

[30] Foreign Application Priority Data

Jul. 15, 1991 [JP] Japan .................. 3-174056

[51] Int. Cl.$^5$ .................................. A61L 2/20
[52] U.S. Cl. ...................... 422/28; 422/292; 422/27
[58] Field of Search .................. 422/27, 28, 292; 53/425, 426

[56] References Cited

U.S. PATENT DOCUMENTS

| | | | |
|---|---|---|---|
| 4,250,143 | 2/1981 | Bryan et al. | 422/27 |
| 4,447,399 | 5/1984 | Runnells et al. | 422/27 |
| 4,734,268 | 3/1988 | Redding et al. | 422/28 |
| 4,744,951 | 5/1988 | Cummings et al. | 422/28 |
| 4,797,255 | 1/1989 | Hatanaka et al. | 422/28 |
| 4,952,370 | 8/1990 | Cummings et al. | 422/27 |

FOREIGN PATENT DOCUMENTS

| | | |
|---|---|---|
| 0114619 | 7/1987 | European Pat. Off. |
| 0257668 | 3/1988 | European Pat. Off. |
| 0384535 | 8/1990 | European Pat. Off. |

*Primary Examiner*—Timothy M. McMahon
*Assistant Examiner*—Hien Tran
*Attorney, Agent, or Firm*—Armstrong, Westerman, Hattori, McLeland & Naughton

[57] ABSTRACT

The hydrogen peroxide gas supplying apparatus to be sterilized by the method of the invention comprises a hydrogen peroxide gas transport air pipe extending from an air source to the location of the article to be sterilized by way of a closed gasifying tank having a heater incorporated therein, and a microorganism removing filter provided on the air pipe and positioned upstream from the gasifying tank. The apparatus is sterilized by supplying an aqueous solution of hydrogen peroxide to the gasifying tank while supply of air from the air source to the air pipe is discontinued so that the solution is gasified by being heated with the heater.

6 Claims, 1 Drawing Sheet

METHOD OF STERILIZING APPARATUS FOR SUPPLYING HYDROGEN PEROXIDE GAS

BACKGROUND OF THE INVENTION

The present invention relates to a method of sterilizing an apparatus for supplying hydrogen peroxide gas for sterilizing the articles, such as containers, to be sterilized in an aseptic filling machine.

Aseptic filling machines are generally provided with an apparatus for supplying hydrogen peroxide gas for sterilizing containers. This apparatus comprises a hydrogen peroxide gas transport air pipe extending from an air source to the location of the article to be sterilized by way of a closed gasifying tank having a heater incorporated therein, and a microorganism removing filter provided on the air pipe and positioned upstream from the gasifying tank.

While the supplying apparatus is out of operation, the interior of the apparatus becomes contaminated with microorganisms in the atmosphere as is already known, whereas it is generally thought unnecessary to sterilize the contaminated apparatus because the contamination is very slight and further because the interior is held in an atmosphere of sterilizing agent.

With aseptic filling machines, the level of sterilization rises every year. Accordingly, the microorganisms present in the apparatus, even if in a very small amount, should be destroyed. Especially if the supply of transport air is started before the start of gasification of aqueous hydrogen peroxide solution when the apparatus is initiated into operation, it is likely that the contaminants within the air pipe will be transported directly to the location of containers.

SUMMARY OF THE INVENTION

The main object of the present invention is to provide a method of sterilizing the hydrogen peroxide gas supplying apparatus as installed as an existing apparatus without necessitating particular additional equipment.

According to the present invention, a hydrogen peroxide gas supplying apparatus of the construction described above is sterilized by supplying an aqueous solution of hydrogen peroxide to the gasifying tank while supply of air from the air source to the air pipe is discontinued so that the solution is gasified by being heated with the heater.

It is desired to close the outlet of the gasifying tank and to open the air pipe to the atmosphere at a position upstream from the filter before the solution of hydrogen peroxide is supplied to the gasifying tank.

With the sterilizing method of the present invention, an aqueous solution of hydrogen peroxide is supplied to the gasifying tank with the supply of air from the air source to the air pipe discontinued so that the solution will be gasified by being heated with the heater. The solution of hydrogen peroxide supplied to the tank is therefore gasified and expanded, and hydrogen peroxide gas diffuses from the tank into the air pipe to sterilize the interior of the air pipe and the filter. With the apparatus in service as an existing apparatus, the air pipe and the filter can be sterilized without necessitating additional means.

Before the aqueous solution of hydrogen peroxide is supplied to the gasifying tank, the outlet of the tank is closed and the air pipe is opend to the atmosphere at a position upstream from the filter. The hydrogen peroxide gas then diffuses from the tank only upstream, whereby the air pipe and the filter upstream from the tank are concentrically sterilized. Consequently, the portions which are especially susceptible to contamination can be sterilized efficiently.

DESCRIPTION OF THE PREFERRED EMBODIMENT

Figure 1:
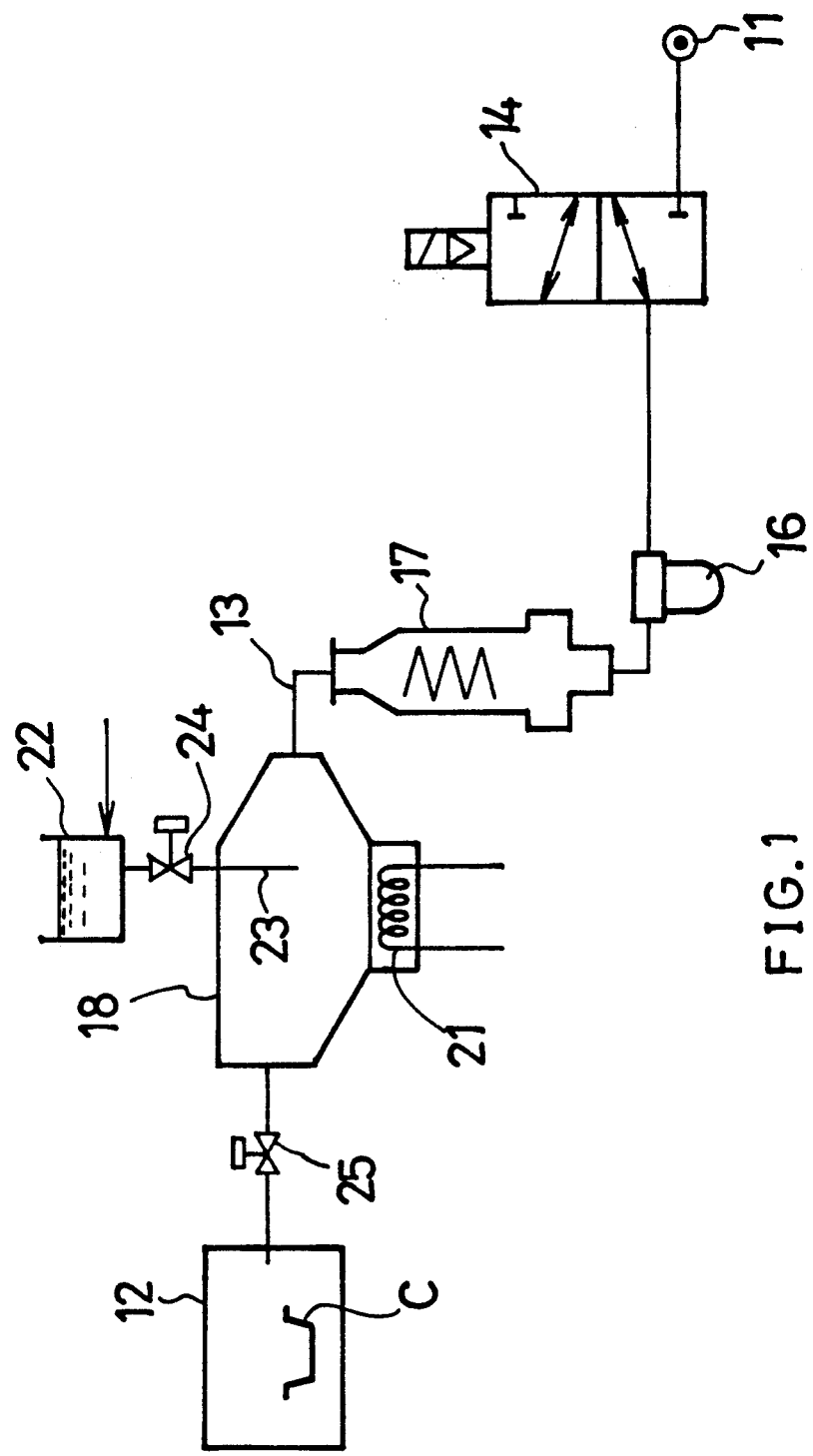
FIG. 1 is a diagram showing the construction of an apparatus for use in the method of the invention.

An embodiment of the invention will be described below with reference to the drawing.

FIG. 1 shows an apparatus for supplying hydrogen peroxide gas for the use of the gas.

The apparatus comprises a hydrogen peroxide gas transport air pipe 13 extending from an air source 11 to a location close to the container C to be sterilized in an aseptic chamber 12. The air pipe 13 is provided with a change-over valve 14, a filter 16 for removing microorganisms, an air heater 17 and a gasifying tank 18 which are arranged at increasing distance away from the air source 11. The gasifying tank 18 is of the closed type and has a heater 21 incorporated therein. Disposed above the tank 18 is a tank 22 containing an aqueous solution of hydrogen peroxide. A supply pipe 23 has one end connected to the solution tank 22 and the other end extending into the gasifying tank 18. The supply pipe 23 is provided with a flow regulating valve 24. The gasifying tank 18 has an outlet provided with a shut-off valve 25.

During steady-state operation, the shut-off valve 25 is left open. Through the air pipe 13, pressurized air is sent from the air source 11 to the filter 16 by way of the change-over valve 14, freed from microorganisms by the filter 16, then heated by the air heater 17 and led into the gasifying tank 18. Through the supply pipe 23, the aqueous solution of hydrogen peroxide is supplied to the gasifying tank 18 at a constant rate and gasified by being heated with the heater 21. The hydrogen peroxide gas produced in the tank 18 is transported to the location of the container C, as entrained in the heated air sent into the gasifying tank 18.

The air pipe 13 is sterilized by the following procedure. The pipe is sterilized usually during the cessation of operation before the apparatus is initiated into steady-state operation.

During the cessation of operation, the changeover valve 14 holds the air pipe 13 open to the atmosphere, and the supply of air from the air source 11 is discontinued. The shut-off valve 25 is usually left open unless otherwise necessary. In this state, the shut-off valve 25 is closed first. Before or after this, the gasifying heater 21 is heated to a temperature permitting gasification. After the heater 21 has been heated to the specified temperature, the aqueous solution of hydrogen peroxide is supplied to the gasifying tank 18 through the supply pipe 23 and applied dropwise to the heater 21 for heating and gasification. This produces an expanded gas, which spontaneously diffuses from the inlet of the tank 18 into the air pipe 13 toward the filter 16. The apparatus is maintained in this state for several minutes, whereby the portion of the air pipe 13 upstream from the tank 18, especially the portion including the filter 16 which needs to be sterilized, is sterilized.

What is claimed is:

1. A method of sterilizing comprising:

providing a hydrogen peroxide gas supplying apparatus having an air supply conduit extending from an air source to a gasifying tank via a microorganism removing filter, the gasifying tank in fluid communication with an aseptic chamber having an interior for sterilizing articles;

discontinuing the supply of air from the air source to the gasifying tank;

supplying hydrogen peroxide to the gasifying tank and heating the hydrogen peroxide supplied to the gasifying tank with a heater incorporated within the gasifying tank so that the hydrogen peroxide is gasified and passes into the air supply conduit for the sterilization thereof;

supplying air from the air source to the gasifying tank through the sterilized air supply conduit;

supplying hydrogen peroxide to the gasifying tank, heating the hydrogen peroxide supplied to the gasifying tank with the gasifying tank heater so that the hydrogen peroxide is gasified and mixes with the air supplied to the gasifying tank from the air source; and passing the mixed gasified hydrogen peroxide and air supplied from the air source to the aseptic chamber in fluid communication with the gasifying tank for sterilizing the interior of the aseptic chamber including any articles therein.

2. The method of sterilizing according to claim 1, further comprising:

prior to the step of gasifying hydrogen peroxide for passing into the air supply conduit, closing a shut off valve disposed between the gasifying tank and the aseptic chamber, and opening the air supply conduit to the atmosphere at a point on an opposite side of the microorganism removing filter from the gasifying tank.

3. The method of sterilizing according to claim 2 wherein the flow of air to the atmosphere at said point on the opposite side, and the supply of air from said air source are controlled by a change-over valve disposed at said opposite side point.

4. The method of sterilizing according to claim 1, wherein in the step of supplying air from the air source to the gasifying tank via the air supply conduit, the air if heated in an air heater disposed between the air source and the gasifying tank so that air supplied from the air source is already heated upon reaching the gasifying tank.

5. The method of sterilizing according to claim 1, wherein in the step of supplying and heating hydrogen peroxide to the gasifying tank for gasifying and mixing with air from the air source, the heater of the gasifying tank is heated prior to the introduction of hydrogen peroxide into the gasifying tank.

6. The method of sterilizing according to claim 4, wherein in the step of gasifying hydrogen peroxide for passing into the air supply conduit for sterilization thereof, the air heater disposed in the air supply conduit is sterilized.

* * * * *